(12) United States Patent
Kumar et al.

(10) Patent No.: US 10,330,587 B2
(45) Date of Patent: Jun. 25, 2019

(54) SMART ELECTROCHEMICAL SENSOR FOR PIPELINE CORROSION MEASUREMENT

(71) Applicants: Amit Kumar, Houston, TX (US); Sanket K. Desai, Bridgewater, NJ (US)

(72) Inventors: Amit Kumar, Houston, TX (US); Sanket K. Desai, Bridgewater, NJ (US)

(73) Assignee: ExxonMobil Upstream Research Company, Spring, TX (US)

( * ) Notice: Subject to any disclaimer, the term of this patent is extended or adjusted under 35 U.S.C. 154(b) by 134 days.

(21) Appl. No.: 15/189,032

(22) Filed: Jun. 22, 2016

(65) Prior Publication Data

US 2017/0059473 A1    Mar. 2, 2017

Related U.S. Application Data

(60) Provisional application No. 62/212,297, filed on Aug. 31, 2015.

(51) Int. Cl.
*G01N 17/02* (2006.01)
*G01N 27/06* (2006.01)
*G01N 17/04* (2006.01)

(52) U.S. Cl.
CPC ............ *G01N 17/02* (2013.01); *G01N 17/04* (2013.01); *G01N 27/06* (2013.01)

(58) Field of Classification Search
CPC ................................ G01N 17/02; G01N 17/04
See application file for complete search history.

(56) References Cited

U.S. PATENT DOCUMENTS

| 3,691,819 | A | * | 9/1972 | Guest | G01M 3/005 346/33 P |
| 4,399,871 | A | * | 8/1983 | Adkins | E21B 34/06 137/539.5 |
| 4,495,808 | A | * | 1/1985 | Fischer, III | E21B 23/10 33/544.3 |
| 4,842,074 | A | * | 6/1989 | Hines | E21B 34/10 166/149 |
| 4,988,389 | A | * | 1/1991 | Adamache | E21B 36/04 166/105 |
| 5,275,038 | A | * | 1/1994 | Sizer | E21B 17/203 340/854.7 |
| 5,517,851 | A | | 5/1996 | Berthold et al. | 73/87 |

(Continued)

FOREIGN PATENT DOCUMENTS

| EP | 1086336 | 9/2002 | ............ F17D 3/00 |
| GB | 2338307 | 12/1999 | ............ G01N 17/00 |

(Continued)

*Primary Examiner* — John Fitzgerald
(74) *Attorney, Agent, or Firm* — ExxonMobil Upstream Research Company-Law Department

(57) ABSTRACT

A method of monitoring a pipeline, comprising positioning a probe device in the pipeline, passing the probe device along the pipeline, collecting at least one fluid sample at each of a plurality of locations along a length of the pipeline, passing each fluid sample into the probe device, and measuring at least one corrosion-related parameter of a fluid at a plurality of locations along the pipeline, wherein the at least one corrosion-related parameter is selected from a group consisting of: pH, temperature, pressure, viscosity, conductivity, salinity, deposits, and corrosivity.

7 Claims, 1 Drawing Sheet

(56) References Cited

U.S. PATENT DOCUMENTS

| | | | | |
|---|---|---|---|---|
| 5,583,426 A * | 12/1996 | Tiefnig | G01N 17/00 204/404 |
| 6,062,311 A * | 5/2000 | Johnson | E21B 7/18 166/223 |
| 6,128,949 A * | 10/2000 | Kleinberg | E21B 49/081 166/250.01 |
| 6,248,700 B1 * | 6/2001 | Vollmer | C09K 8/06 252/387 |
| 6,364,991 B1 * | 4/2002 | Rice | B29C 63/34 156/275.5 |
| 6,431,270 B1 * | 8/2002 | Angle | E21B 4/18 166/50 |
| 6,487,518 B1 | 11/2002 | Miyazaki et al. | 702/170 |
| 6,527,869 B1 * | 3/2003 | Bourg | B08B 9/0551 134/1 |
| 6,644,848 B1 | 11/2003 | Clayton et al. | 374/7 |
| 6,722,442 B2 * | 4/2004 | Simpson | E21B 23/00 166/173 |
| 6,871,713 B2 | 3/2005 | Meister et al. | |
| 6,919,729 B2 * | 7/2005 | Tiefnig | G01N 17/00 324/700 |
| 6,939,717 B2 * | 9/2005 | Jiang | E21B 47/011 436/121 |
| 7,051,587 B2 * | 5/2006 | Simpson | B08B 9/049 73/152.54 |
| 7,062,958 B2 * | 6/2006 | Diakonov | E21B 49/081 166/264 |
| 7,282,928 B1 | 10/2007 | Hladky et al. | 324/700 |
| 7,363,972 B2 * | 4/2008 | Dybdahl | E21B 49/081 166/250.01 |
| 7,440,283 B1 * | 10/2008 | Rafie | E21B 47/011 165/185 |
| 7,665,519 B2 * | 2/2010 | Oddie | E21B 49/08 166/162 |
| 7,818,156 B2 | 10/2010 | Vachhani et al. | 703/12 |
| 7,895,891 B2 * | 3/2011 | Prieto Barranco | B01D 5/0042 73/304 C |
| 7,941,282 B2 | 5/2011 | Ziegel et al. | 702/34 |
| 8,360,635 B2 | 1/2013 | Huang et al. | 374/147 |
| 8,447,529 B2 | 5/2013 | Hernandez et al. | 702/25 |
| 8,519,713 B2 * | 8/2013 | Lawrence | G01N 33/2841 324/324 |
| 8,564,315 B2 * | 10/2013 | Fisseler | G01N 17/02 166/250.01 |
| 9,005,983 B2 * | 4/2015 | McGuinness | G01N 33/24 436/182 |
| 9,637,440 B2 * | 5/2017 | Crawford | H01G 11/32 |
| 2003/0057401 A1 * | 3/2003 | Craig | C09D 5/08 252/387 |
| 2003/0121338 A1 | 7/2003 | Yates | 73/865.8 |
| 2003/0134426 A1 * | 7/2003 | Jiang | E21B 47/011 436/121 |
| 2003/0206026 A1 * | 11/2003 | Diakonov | E21B 49/08 324/723 |
| 2004/0050548 A1 * | 3/2004 | Dybdahl | E21B 49/081 166/264 |
| 2005/0029125 A1 * | 2/2005 | Jiang | E21B 49/082 205/775 |
| 2005/0168208 A1 | 8/2005 | Pots et al. | |
| 2006/0243603 A1 * | 11/2006 | Jiang | E21B 47/00 205/775 |
| 2007/0119244 A1 | 5/2007 | Goodwin et al. | |
| 2007/0193357 A1 | 8/2007 | Daaland et al. | 73/626 |
| 2007/0256942 A1 * | 11/2007 | Atherton | E21B 47/00 205/775.5 |
| 2008/0023328 A1 * | 1/2008 | Jiang | E21B 47/10 204/407 |
| 2008/0066908 A1 * | 3/2008 | Oddie | E21B 49/08 166/264 |
| 2009/0223672 A1 * | 9/2009 | Naik | F16L 55/46 166/344 |
| 2009/0308656 A1 * | 12/2009 | Chitwood | E21B 4/04 175/40 |
| 2010/0108314 A1 * | 5/2010 | Oddie | E21B 49/08 166/264 |
| 2010/0148780 A1 * | 6/2010 | Lawrence | G01N 27/4045 324/324 |
| 2010/0162503 A1 * | 7/2010 | Rosen | B08B 9/035 15/104.061 |
| 2012/0064632 A1 * | 3/2012 | Robinson | G01N 33/24 436/79 |
| 2012/0132544 A1 * | 5/2012 | Lawrence | G01N 27/302 205/782 |
| 2012/0255933 A1 * | 10/2012 | McKay | B08B 9/02 219/61 |
| 2012/0279599 A1 | 11/2012 | Gluskin et al. | 138/97 |
| 2013/0304680 A1 | 11/2013 | Bailey et al. | 706/15 |
| 2014/0005995 A1 | 1/2014 | O'Connor et al. | 703/9 |
| 2014/0081594 A1 | 3/2014 | Tunheim et al. | 702/150 |
| 2014/0212978 A1 | 7/2014 | Sharpe, Jr. et al. | 436/6 |
| 2014/0246574 A1 * | 9/2014 | Pope | E21B 47/102 250/269.1 |
| 2014/0278148 A1 | 9/2014 | Ziegel et al. | 702/34 |
| 2014/0283876 A1 * | 9/2014 | Fjerdingstad | B08B 9/0535 134/8 |
| 2014/0332398 A1 * | 11/2014 | Lawrence | G01N 27/302 205/333 |
| 2015/0034198 A1 * | 2/2015 | Cheatham, III | F16L 55/163 138/97 |
| 2015/0122364 A1 * | 5/2015 | Cheatham, III | F16L 55/1283 138/98 |
| 2015/0204820 A1 * | 7/2015 | Mayo | G01N 29/348 73/632 |
| 2015/0217323 A1 * | 8/2015 | Broze | B08B 9/0557 427/239 |
| 2015/0268153 A1 * | 9/2015 | Johannes Jacobus Maria | G01N 17/04 205/775.5 |
| 2016/0131297 A1 * | 5/2016 | Cheatham, III | F16L 55/163 138/97 |
| 2017/0307126 A1 * | 10/2017 | Cheatham, III | F16L 55/1283 |

FOREIGN PATENT DOCUMENTS

| | | | |
|---|---|---|---|
| WO | WO2009/052235 | 4/2009 | E21B 49/10 |
| WO | WO2013/169241 | 11/2013 | G01N 17/00 |
| WO | WO2014/005126 | 1/2014 | G01N 29/34 |
| WO | WO2014/073969 | 5/2014 | G01N 17/04 |
| WO | WO2014/142825 | 9/2014 | G06N 7/00 |
| WO | WO2014/167285 | 10/2014 | G01B 17/02 |

* cited by examiner

SMART ELECTROCHEMICAL SENSOR FOR PIPELINE CORROSION MEASUREMENT

CROSS-REFERENCE TO RELATED APPLICATIONS

This application claims the priority benefit of U.S. Patent Application 62/212,297 filed Aug. 31, 2015 entitled SMART ELECTROCHEMICAL SENSOR FOR PIPELINE CORROSION MEASUREMENT, the entirety of which is incorporated by reference herein.

BACKGROUND

Ensuring the integrity of oil and gas transport pipelines is a significant focus of the energy industry. Loss of integrity can result in significant adverse financial and environmental impact. Operating experience has shown that internal corrosion is the one of the main threats to pipeline integrity for flowlines and gathering lines carrying untreated produced fluids. The fluids transported through the pipelines may be inherently corrosive and may rapidly reduce the pipe wall thickness, thereby increasing the risk of a loss of pipeline integrity. Consequently, pipeline inspection and pipeline corrosion measurement are of importance to the industry.

Currently, the industry uses two types of corrosion detection sensors: movable and fixed. Movable pipeline inspection tools include tools such as in-line-inspection (ILI) tools or smart pigs travel inside the pipeline with fluid to assess the condition of pipelines. These tools may be equipped with sensors that measure the remaining wall thickness on the pipeline. The data provided by such inspection, however, is a lagging indicator of corrosion; corrosion must first occur and the wall thickness must first be reduced before corrosion may be detected. Furthermore, the time period between two consecutive inspections runs may be relatively long (e.g., more than 5 years), and substantial damage may progress in the interim. Early detection of corrosion would enable earlier corrective actions, more timely corrosion mitigation and/or intervention, and elimination and/or reduction of high consequence integrity loss events.

Fixed sensors may also be used for corrosion detection and/or measurement. Installation of fixed sensors or coupons along the pipeline length may provide real-time monitoring of pipeline conditions. Currently, corrosion coupons and/or corrosion rate measuring probes such as Electrical Resistance (ER) and Linear polarization Resistance (LPR) are used to measure corrosion rate in real-time, or at frequent interval in the pipeline at fixed location. These in-pipeline coupons/probes are only capable of providing corrosion information at a local point. However, pipeline corrosion may vary with location along the length due to topography and change in flow conditions in the pipeline. If fixed sensors are installed at a relatively less corrosive location in the pipeline, the sensors may present an inaccurate picture of the state of the pipeline. Identification of correct installation location may be critical in extracting appropriate information from these fixed sensors, but such information may be difficult to obtain. Consequently, a large number of such sensors may need to be mounted along the length of the pipeline to get accurate information on the state of the full pipeline.

Prior art technologies include U.S. Patent Publication No. 2003/0121338 for a pipeline pigging device for non-destructive inspection of the fluid environment in a pipeline. This disclosure includes a spherical, flowing fluid monitoring tool wherein the sensing element is at/near the surface of the sphere for directly measures the fluid characteristics as it flows along the line. Another prior art technology includes U.S. Patent Publication No. 2012/0279599 for an infrastructure corrosion analysis. This disclosure includes a pig-like device that collects pipeline wall corrosion data from a pipeline, analyzes the data, evaluates corrosion risk, and creates an implementation plan for the remediation of the pipeline. Still another prior art technology includes U.S. Pat. No. 7,282,928 for a corrosion measurement field device with improved harmonic distortion analysis (HDA), linear polarization resistance measurement (LPR), electrochemical noise measurement (ECN) capability. This disclosure includes a corrosion measurement device that measures corrosion of a structure exposed to a fluid using a multi-electrode system and where a sinusoidal signal is transmitted into the fluid through one electrode and response evaluated using a second electrode.

Consequently, there exists a need for a sensor that is capable of providing early detection of pipeline corrosion without relying on an ex post facto corrosion analysis. There also exists a need for a sensor that is capable of providing corrosion information along a length of a pipeline without regard to topography and/or change in flow conditions in the pipeline. There further exists a need for a sensor that can provide accurate and timely information about the state of a pipeline.

SUMMARY

One embodiment includes a method of monitoring a pipeline, comprising positioning a probe device in the pipeline, passing the probe device along the pipeline, collecting at least one fluid sample at each of a plurality of locations along a length of the pipeline, passing each fluid sample into the probe device, and measuring at least one corrosion-related parameter of a fluid at a plurality of locations along the pipeline, wherein the at least one corrosion-related parameter is selected from a group consisting of: pH, temperature, pressure, viscosity, conductivity, salinity, deposits, and corrosivity.

Another embodiment includes an apparatus for monitoring a pipeline, comprising an electrochemical sensor device comprising: a body configured for passage along the pipeline, a fluid inlet on the electrochemical sensor device configured to collect at least one sample of a fluid, an electrochemical sensor disposed within the body and coupled to the fluid inlet, wherein the electrochemical sensor is configured to measure at least one corrosion-related parameter of the at least one sample.

Still another embodiment includes an apparatus for measuring a fluid in a pipeline, comprising a probe device, comprising a fluid sample collection section configured to collect at least one fluid sample, a fluid sample analysis section configured to analyze the fluid sample, a fluid sample disposal section configured to dispose of the fluid sample, wherein the probe device is configured for passage down the pipeline from a first location to a second location.

Unlike U.S. Patent Publication No. 2003/0121338, in some embodiments the present disclosure may not conduct measurements directly in the fluid. In disclosed embodiments, the fluid may be collected in a small reservoir in the tool and/or the sensor may be internally disposed. Unlike U.S. Patent Publication No. 2012/0279599, in some embodiments the present disclosure may not involve monitoring pipeline wall thickness and/or may only involve monitoring one or more corrosivity characteristics and/or parameters of the fluid. Unlike U.S. Pat. No. 7,282,928, in some embodiments the present disclosure may not rely on transmitting a sinusoidal signal into the fluid for generating a response. Instead, disclosed embodiments may use a direct (non-oscillating) signal to generate a response. Unlike WO2014073969A2, in some embodiments the present disclosure may deploy the existing LPR and ER probe technologies on a pig/robot which can travel in the pipeline. Therefore, the probes are not fixed to the equipment. Furthermore, our invention focuses on deploying suit of sensors in the pipeline to retrieve the information along the whole pipeline as they move through it.

BRIEF DESCRIPTION OF THE DRAWINGS

The advantages of the present techniques are better understood by referring to the following detailed description and the attached drawings, in which.

DETAILED DESCRIPTION

Figure 1:
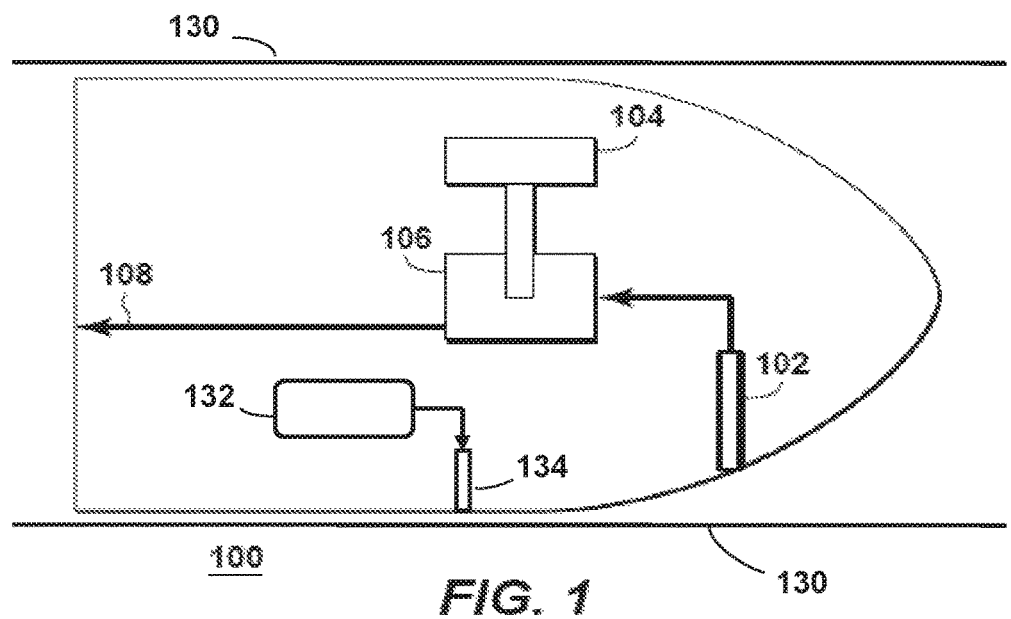
FIG. 1 is a schematic diagram of a first embodiment of a smart electrochemical sensor device for pipeline corrosion measurement.

In the following detailed description section, specific embodiments of the present techniques are described. However, to the extent that the following description is specific to a particular embodiment or a particular use of the present techniques, this is intended to be for exemplary purposes only and simply provides a description of the exemplary embodiments. Accordingly, the techniques are not limited to the specific embodiments described herein, but rather, include all alternatives, modifications, and equivalents falling within the true spirit and scope of the appended claims.

At the outset, for ease of reference, certain terms used in this application and their meanings as used in this context are set forth. To the extent a term used herein is not defined herein, it should be given the broadest definition persons in the pertinent art have given that term as reflected in at least one printed publication or issued patent. Further, the present techniques are not limited by the usage of the terms shown herein, as all equivalents, synonyms, new developments, and terms or techniques that serve the same or a similar purpose are considered to be within the scope of the present claims.

As used herein, the term "fluid" may refer to gases, liquids, and/or combinations of gases and liquids, as well as to combinations of liquids and solids, and particularly to hydrocarbons.

As used herein, the term "hydrocarbon" refers to an organic compound that primarily includes the elements hydrogen and carbon, although nitrogen, sulfur, oxygen, metals, or any number of other elements may be present in small amounts. As used herein, hydrocarbons generally refer to components found in natural gas, oil, or chemical processing facilities.

As used herein with respect to fluid processing equipment, the term "inline" means sequentially within an identifiable common axis of orientation of flow.

As used herein, the term "substantial" when used in reference to a quantity or amount of a material, or a specific characteristic thereof, refers to an amount that is sufficient to provide an effect that the material or characteristic was intended to provide. The exact degree of deviation allowable may depend, in some cases, on the specific context.

As used herein, the terms "a" and "an," mean one or more when applied to any feature in embodiments of the present inventions described in the specification and claims. The use of "a" and "an" does not limit the meaning to a single feature unless such a limit is specifically stated.

As used herein, the definite article "the" preceding singular or plural nouns or noun phrases denotes a particular specified feature or particular specified features and may have a singular or plural connotation depending upon the context in which it is used.

This disclosure comprises mounting one or more sensing probes, e.g., LPR probes, on a device configured to travel along a pipeline and gather fluid corrosivity information. LPR allows corrosion-related metrics or parameters to be measured directly in real-time. The operating principle of LPR is based on measuring the flow of current between electrodes. When a metal/alloy electrode is immersed in an electrolytically conducting fluid of sufficient oxidizing power, it will corrode by an electrochemical mechanism. At anodic sites, metal will pass from the solid surface into the adjacent solution and, in so doing, leave a surplus of electrons at the metal surface. The excess electrons will flow to nearby sites, referred to as cathodic sites, where the excess electrons may be consumed by oxidizing species from the corrosive liquid. The corrosion current, i.e., the current generated by the flow of electrons from anodic to cathodic sites, may be used to compute a corrosion rate using a modified version of Faraday's Law. This disclosure may include distributing LPR probes around a device circumference to sample fluid and passing the device inline along a pipeline to sample different locations in the pipeline.

This disclosure includes a sensor capable of providing early detection of pipeline corrosion without relying on an ex post facto corrosion analysis, e.g., by sampling the fluid and not the pipeline wall. This disclosure includes a sensor capable of providing corrosion information along a length of a pipeline without regard to topography and/or change in flow conditions in the pipeline, e.g., by periodically obtaining samples at predetermined intervals along a length of pipeline and not remaining fixed. This disclosure includes a sensor that can provide accurate and timely information about the state of a pipeline, e.g., by providing real-time information about corrosive fluid conditions and/or parameters within a pipeline.

FIG. 1 is a schematic diagram of a first embodiment of a smart electrochemical sensor device or probe device 100 for pipeline corrosion measurement. The device 100 may have a body diameter that is substantially the same diameter as the pipeline 130. The device 100 may have at least a portion of the body having a substantially cylindrical shape. The device 100 may have a conical first end similar to that of conventional cleaning pigs. Those of skill in the art will appreciate that suitable alternate embodiments are envisioned having differing shapes and/or diameters to create the desired flow characteristics, e.g., having fins, ridges, dimples, tails, etc., having a generally torpedo shape, a generally spherical shape, a generally oblate spheroid shape, a generally prolate spheroid shape, etc. Additionally, some embodiments may comprise propulsion mechanisms, e.g., propellers, jets, etc., on a second end distal from the first end for propelling or accelerating the passage of the device along a pipeline. Other propulsion mechanisms may permit the device 100 to roll, e.g., using gravity or drive wheels. Other embodiments may comprise drag mechanisms, e.g., parachutes, fins, rudders, ribs, etc., for slowing the passage of the device 100 in the pipeline and/or maintaining suitable orientation/alignment of the device in the pipeline.

The device 100 comprises an inlet port 102 in a fluid sample collection section for collecting a fluid sample. In some embodiments, the port 102 may be wire framed with/without spring-loaded components, e.g., arms, flaps, caps, etc., for restricting sampling periods, e.g., limiting sampling to predetermined times, periodicities, locations, etc. The port 102 is depicted on a radially inwardly disposed location on a conical head end of the device 100 in order to collect a sample of fluid that is (1) substantially in front of the device 100, (2) relatively close to the pipeline wall, and (3) generally representative of the fluid passing along the pipeline wall (not depicted). Other locations for the port 102 may be suitably employed within the scope of this disclosure to obtain the desired fluid sample characteristics as would be understood by those of skill of the art and are considered within the scope of this disclosure. Some embodiments may utilize filters, screens, baffles, or other mechanisms disposed on or in conjunction with the port 102 to obtain a representative sample suitably representative of the fluid for which sampling is desired.

An internally disposed power source 104 is coupled to an LPR probe 106 in a fluid sample analysis section of the device 100. The port 102 is coupled to and configured to pass a fluid sample to the LPR probe 106. An outlet port 108 is coupled to the LPR probe 106 and is configured to dispose of a fluid sample following sampling at the LPR probe 106, e.g., via an internally disposed passage having an outlet located in a fluid sample disposal section positioned at a second tail end of the device 100. In some embodiments, the outlet port 108 is configured to act as or in conjunction with a propulsion mechanism as discussed above, e.g., by positioning the outlet port 108 such that the outlet port 108 emits a propulsion fluid between the device 100 and a pipeline wall (not depicted). While depicted as having a singular internal sampling system, other embodiments may include a plurality of internal sampling systems sharing the same ports 102, 108, LPR probe 106, and/or power source 104 or having one or more such components configured to operate independently, e.g., for redundancy, for sampling different fluids and/or corrosion-related parameters, etc., within the scope of this disclosure.

In operation, the device 100 may be positioned in a pipeline at a first location. The device 100 may pass along a pipeline and may collect one or more fluid samples via the outlet port 108. The fluid samples may pass to the LPR probe 106 where each of the fluid samples may be measured for at least one corrosion-related parameter, e.g., pH, temperature, pressure, viscosity, conductivity, salinity, deposits, corrosivity, etc., that may be used to determine a corrosion index for the pipeline. In LPR, the measurements may show decay characteristic, e.g., due to capacitive effects. This delay or time lag may vary depending on the specific characteristics of the metal/environment system. Since the decay characteristic is asymptotic, systems with 'capacitive inertia' may closely approach equilibrium in 0-5 minutes, 0-10 minutes, 0-15 minutes, 0-30 minutes, 5-10 minutes, 5-15 minutes, 5-30 minutes, 10-15 minutes, 10-30 minutes, or 15-30 minutes. Frequency of sampling and measurement may be varied based on the properties of the fluid to be sampled and/or measured parameters and may be optimized using a control system configured to control the sampling frequency, e.g., by controlling the opening/closing frequency of the ports 102 and/or 108 based on a timer, a location, or another metric to obtained the desired operating characteristics for the device 100. In some embodiments, the device 100 may be equipped with components configured to periodically clean the LPR probe 106 either chemically or mechanically depending on fluid properties to avoid fouling of sensors. The device 100 may be removed from the pipeline at a second location, e.g., downstream along a pipeline. The second location may be remote from the first location by a separation of between 0-1 kilometers (km), 0-10 km, 0-50 km, 0-100 km, 10-50 km, 10-100 km, 50-100 km, a distance greater than 1 km, 10 km, 50 km, or 100 km, as optionally determined, e.g., based on the power available to the power source 104, based on global positioning system (GPS) availability, based on topological and/or geographic limitations, etc.

In some embodiments, the device 100 may further comprise a chemical dispersing section configured to disperse a chemical, e.g., a corrosion inhibiting chemical, into the pipeline, e.g., in response to a parameter measurement exceeding a predetermined set point. The chemical dispersing section is comprised of a chemical reservoir 132 configured to retain a corrosion inhibiting chemical and a chemical dispensing port 134 coupled to the chemical reservoir, and configured to dispense the corrosion inhibiting chemical into the pipeline. The device may dispose corrosion inhibitor or biocide if the residual of corrosion inhibitor or biocide is below threshold. Threshold value of corrosion inhibitor is defined based on fluid corrosivity or corrosion rate at that location which depends on the corrosion allowance used during pipeline design. Typical value of threshold corrosion rate may be lower than 20 mils per year (mpy), e.g., between 0-20 mpy, 0-10 mpy, 0-5 mpy, etc. Suitable corrosion inhibitors may include chemicals such as quaternary ammonium salt, quaternary amine, imidazoline, or other similar compounds. In some cases, emulsifier may be added in the fluid to remove free water, or pH buffering agent may be added to maintain pH at desired value in the pipeline.

In some embodiments, the device 100 may further comprises one or more location sensors, e.g., a GPS sensor, for determining the position of the device 100. The device 100 may further comprise computer equipment configured to record the location of the device 100 at a particular time, e.g., in order to record particular regions of concern within the pipeline for future monitoring, in order to disperse corrosion inhibiting chemicals, etc.

Figure 2:
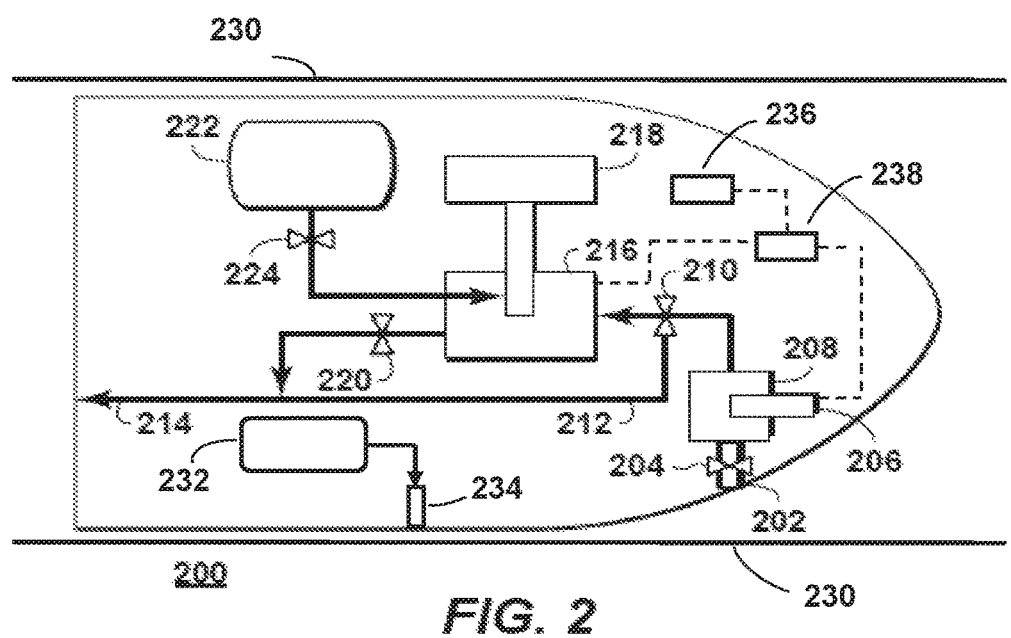
FIG. 2 is a schematic diagram of a second embodiment of a smart electrochemical sensor device for pipeline corrosion measurement.

FIG. 2 is a schematic diagram of a second embodiment of a smart electrochemical sensor device 200 for pipeline corrosion measurement. The components of the device 200 may be substantially the same as the corresponding components of the device 100 of FIG. 1 except as otherwise noted. The device 200 may have a body diameter that is substantially the same diameter as the pipeline 230. The device 200 has an inlet port 202 and an inlet valve 204 configured to start and stop fluid sample collection, e.g., as directed by a control system (not depicted) configured to control sampling periodicity. A conductivity measuring probe 206 is disposed in a fluid reservoir 208. A three-way valve 210 is configured to pass a fluid sample from the fluid reservoir along a bypass 212 to the outlet port 214 or along an inlet line to the LPR probe 216. An internally disposed power source 218 is coupled to the LPR probe 216. An outlet valve 220 is configured to pass the fluid sample from the LPR probe to the outlet port 214. In some embodiments, the outlet valve 220 is directed by a control system (not depicted) configured to control sampling periodicity. A probe cleaning equipment 222 is disposed in a cleaning section on the device 200 and configured to store a probe cleaning liquid. A cleaning liquid valve 224 is disposed on a line coupling the probe cleaning equipment 222 to the LPR probe 216. In some embodiments, the probe cleaning equipment 222 comprises chemical cleaning equipment, e.g., one or more nozzles and pumps configured to pass the probe cleaning liquid to the LPR probe in order to periodically clean the LPR probe 216 and thus avoid fouling of the sensors. Mechanical cleaning equipment (not depicted) may be disposed on the device 200 and used alternately or additionally for substantially the same purpose as understood by those of skill in the art. The device 200 may further comprise a chemical dispersing section configured to disperse a chemical, e.g., a corrosion inhibiting chemical, into the pipeline, e.g., in response to a parameter measurement exceeding a predetermined set point. The chemical dispersing section is comprised of a chemical reservoir 232 configured to retain a corrosion inhibiting chemical and a chemical dispensing port 234 coupled to the chemical reservoir, and configured to dispense the corrosion inhibiting chemical into the pipeline. The device 200 may further comprise a location sensor 236 and a memory 238 configured to store a location of the electrochemical sensor device in response to measuring at least one corrosion-related parameter, sensing a location of the electrochemical sensor device, or a combination thereof. For clarity, FIGS. 1 and 2 herein are purely schematic in nature and presented to assist in illustrating embodiments of elements disclosed herein. Unless explicitly stated in the specification herein, these figures are not meant in any manner to suggest or limit the physical placement or orientation of any element shown within device 100 or 200.

While the present techniques may be susceptible to various modifications and alternative forms, the exemplary embodiments discussed herein have been shown only by way of example. However, it should again be understood that the techniques disclosed herein are not intended to be limited to the particular embodiments disclosed. Indeed, the present techniques include all alternatives, modifications, combinations, permutations, and equivalents falling within the true spirit and scope of the appended claims.

What is claimed is:

1. An apparatus for monitoring a pipeline, comprising:
    an electrochemical sensor device comprising:
        a body configured for passage along the pipeline;
        a fluid inlet on the electrochemical sensor device configured to collect at least one sample of a fluid;
        a conductivity measuring probe disposed within the body and fluidly coupled to the fluid inlet;
        an LPR probe disposed within the body and fluidly coupled to the conductivity measuring probe, wherein the LPR probe is configured to measure the corrosion rate of the at least one sample;
        a chemical reservoir configured to retain a corrosion inhibiting chemical; and
        a chemical dispensing port coupled to the chemical reservoir, and configured to dispense the corrosion inhibiting chemical into the pipeline in response to the corrosion rate detected by the LPR probe exceeding a predetermined set point.

2. The apparatus of claim 1, wherein the electrochemical sensor device further comprises:
    a location sensor, and a memory configured to store a location of the electrochemical sensor device in response to measuring the corrosion rate, sensing a location of the electrochemical sensor device, or a combination thereof.

3. The apparatus of claim 1, wherein the electrochemical sensor device further comprises:
    a fluid reservoir having a fluid reservoir inlet and a fluid reservoir outlet, wherein the fluid reservoir is configured to retain the sample of the fluid;
    an inlet valve coupled to the fluid reservoir inlet; and
    an outlet valve coupled to the fluid reservoir outlet.

4. The apparatus of claim 1, wherein the electrochemical sensor device further comprises:
    a cleaning fluid reservoir configured to retain a sensor cleaning fluid; and
    a cleaning fluid dispenser coupled to the cleaning fluid reservoir on a first end and coupled to the sensor on a second end, and configured to pass the sensor cleaning fluid from the cleaning fluid reservoir to the sensor.

5. The apparatus of claim 1, wherein the body has a diameter that is substantially the same diameter as the pipeline, and wherein at least a portion of the body has a substantially cylindrical shape.

6. The apparatus of claim 5, wherein the body comprises a conically shaped first end configured to lead the probe device along the pipeline, and wherein the fluid inlet is disposed on the first end of the body.

7. The apparatus of claim 5, wherein the electrochemical sensor device further comprises:
    a propulsion mechanism disposed on a tail end of the electrochemical sensor device.

* * * * *